United States Patent [19]

Henry

[11] Patent Number: 5,106,382
[45] Date of Patent: Apr. 21, 1992

[54] WASHABLE DIAPER WITH A FIXED WATER PROOF COVER

[76] Inventor: Donna Henry, 5162 Marquette Ct., New Berlin, Wis. 53151

[21] Appl. No.: 645,228

[22] Filed: Jan. 24, 1991

[51] Int. Cl.$^5$ .............................................. A61F 13/15
[52] U.S. Cl. ........................... 604/385.2; 604/385.1; 604/391
[58] Field of Search ................... 604/385.1, 385.2, 389, 604/390, 391

[56] References Cited

U.S. PATENT DOCUMENTS

| | | | |
|---|---|---|---|
| 1,989,283 | 1/1935 | Limacher | 604/385.1 X |
| 2,392,620 | 12/1949 | Cohen | 604/395 |
| 3,653,381 | 4/1972 | Warnken | 604/391 |
| 4,022,212 | 5/1977 | Lovison | 604/391 X |
| 4,037,602 | 7/1977 | Hawthorne | 604/390 X |
| 4,402,690 | 9/1983 | Redfern | 604/391 |
| 4,425,128 | 1/1984 | Motomura | 604/381 |
| 4,425,130 | 1/1984 | DesMarais | 604/389 |
| 4,516,975 | 5/1985 | Mitchell | 604/385 |
| 4,704,117 | 11/1987 | Mitchell | 604/391 |
| 4,895,568 | 1/1990 | Enloe | 604/285.2 |
| 5,037,416 | 8/1991 | Allen et al. | 604/385.1 |

FOREIGN PATENT DOCUMENTS

| | | | |
|---|---|---|---|
| 1491234 | 4/1969 | Fed. Rep. of Germany | 604/385.1 |
| 3317117 | 6/1984 | Fed. Rep. of Germany | 604/389 |

*Primary Examiner*—Randall L. Green
*Assistant Examiner*—David H. Willse
*Attorney, Agent, or Firm*—Michael, Best & Friedrich

[57] ABSTRACT

A composite diaper comprising at least two layers, each layer with opposite sides, opposite ends, and opposite surfaces, and where an inner layer is joined to an outer layer only at the layers' opposite ends. The opposite sides of the inner layer remain freely separable from the opposite sides of the outer layer, and the adjacent surfaces of the layers are freely separable from one another, except for the attachments of the inner layer and the outer layer at their opposite ends. The inner layer is formed at least partially of a moisture absorbent textile fabric, while the outer layer is formed of a water resistant fabric.

11 Claims, 2 Drawing Sheets

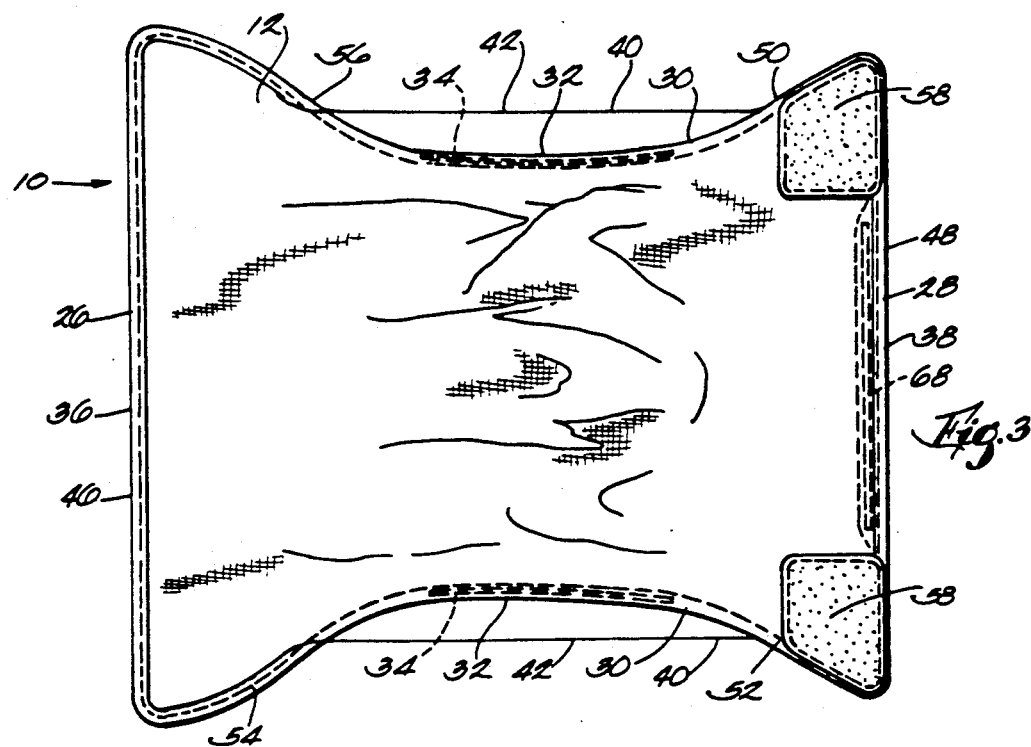
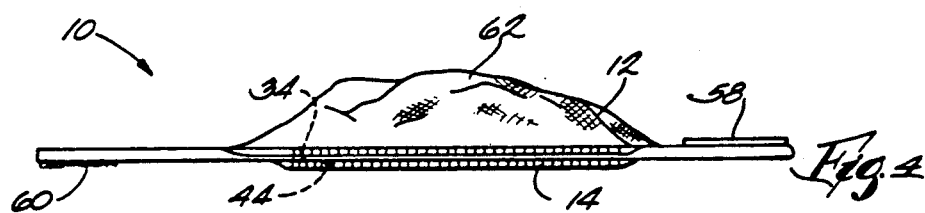
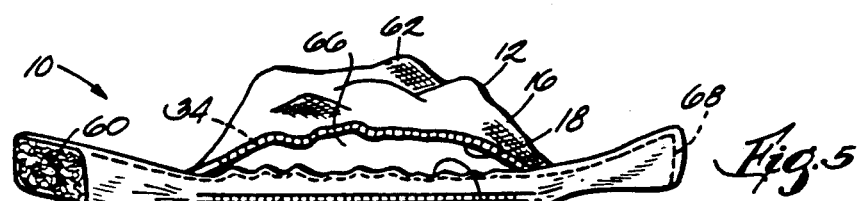
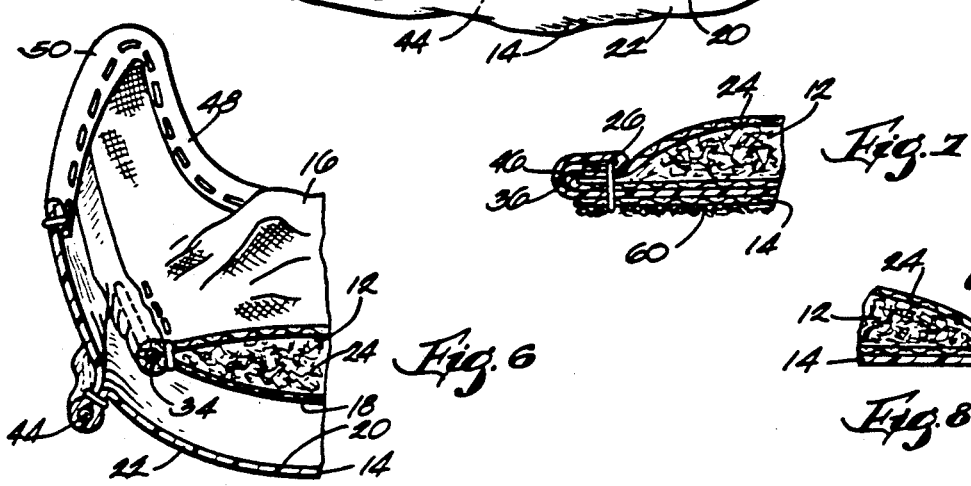
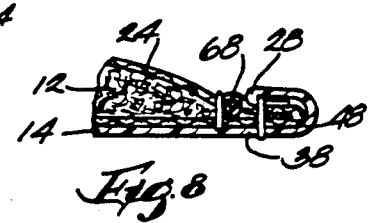

WASHABLE DIAPER WITH A FIXED WATER PROOF COVER

FIELD OF THE INVENTION

This invention relates to diapers, and more particularly, to washable reusable diapers with attached waterproof covers.

BACKGROUND ART

Diapers are commonly comprised of a single piece of cloth, are rectangular in shape, and the cloth fabric used is comprised of fibers of a highly moisture absorbent character. Typically, these diapers are secured by the use of pins. Cloth diapers of this type are strongly absorbent, but not leak-proof, and thus are generally used in concert with waterproof pants made of plastic or some other suitably water resistant material.

Other prior art diapers are designed to be used once and thrown away. They are manufactured using inexpensive materials, and a water proof barrier is commonly affixed during manufacture to the outside of the water absorbent layers of the diaper. In addition to the convenience provided by being disposable, these diapers have the added convenience of not requiring the addition of a separate waterproof layer. Diapers of the disposable variety generally incorporate other convenience features as well, such as coming in a variety of sizes and being provided with strips of tape to secure the diaper.

Although manufactured of relatively inexpensive materials, disposable diapers are actually more expensive to use, being thrown away after a single use. Additionally, disposable diapers create a disposal and environmental waste problem.

Other cloth diapers have included an outer waterproof barrier. The outer water resistant layer incorporated into these diapers makes them more like the disposable diapers in appearance, as well as in their convenience of use. Although such diapers are intended to be reused, the waterproof barrier affixed to the cloth portion is an impediment to washing and drying. The same barrier that makes such a diaper leak-proof also makes it inaccessible to both the wash water and to the air of subsequent drying operations.

U.S. Pat. Nos. 4,402,690, 4,516,975, and U.S. Pat. No. 4,704,117 each disclose examples of reusable diapers that are made of a composite of layers, each diaper having an inner cloth layer or layers of absorbent material, and an outer layer that functions to retain moisture. The diapers are contoured for better fit, and are provided with Velcro type fasteners for ease of attachment, thus requiring relatively simple operation for putting on and removing the diaper.

A diaper as described in these patents has many of the advantages of a disposable diaper, and yet is reusable. Desirable as the added convenience may be, before such a diaper is ready to be used again it must be rinsed, in some cases presoaked, and then washed and dried. The convenience provided by having a waterproof cover permanently attached to the diaper by the manufacturer is purchased at the price of efficiency in both the washing and the drying of the diaper. The moisture retentive barrier sewn on to such a diaper reduces the surface area of the diaper portion, for cleaning and drying purposes, effectively by one-half.

SUMMARY OF THE INVENTION

One of the objects of the present invention is, therefore, to provide a washable and reusable cloth diaper that has the convenience of a disposable diaper, in having a moisture retentive barrier to obviate the necessity of a separate use of water resistant pants over the diaper, but that does not retain certain of the disadvantages of the current designs for such combination diapers.

The present invention provides a reusable cloth diaper that has both an inner cloth layer and an outer layer made of a water resistant fabric. The inner absorbent fabric layer and the outer water resistant fabric layer are attached to one another only at the ends of the diaper, either solely along the edges of the ends, or along those end edges and additionally along edges of portions of the sides of the diaper that are nearest to the ends. The layers of the diaper are otherwise completely separable from one another.

An advantage of a diaper of this design is that the separation of the fabric layers allows for more thorough and efficient cleaning during washing, which necessitates fewer or shorter washes, with resulting savings in time, water and energy. For similar reasons there is more efficient drying as well, which necessitates shorter drying times, with similar savings in time and energy as found in washing of the diaper. By using an inexpensive diaper liner, simple and efficient cleaning is accomplished overall for a diaper of the present construction, relative to composite diapers of previous designs.

The division of the fabric layers makes possible another advantageous design feature, in that the fabric layers can be provided with elastics of varying resiliencies, which can generate additional features to the diaper in fit, comfort or water barrier formation. If the outer layer has elastic of a greater relative resiliency, the inner layer is comparatively looser when the diaper is in a relaxed state. This loose fabric can be pulled up almost as excess fabric, and consequently used to reinforce absorbency. The fabric can be folded and layered forward or rearward, depending on where additional absorbency is desired.

Another advantage provided by the separation of the fabric layers is that the fit of each layer can be adjusted separately. By providing the midportions of the separate layers with elastics of differing lengths, strengths or resilience, various effects can be accomplished, such as providing improved water barrier formation at the sides of the diaper, or in generally improving the fit at the wearer's legs.

The washable and reusable diaper of this invention has all of the ease and convenience in application of a disposable diaper, but with the great enhancement, over other convenient reusable diapers, achieved in cleaning and drying efficiencies. These and other enhanced properties are only made possible by the unique construction of the diaper, which allows for greater breathability and better access to the inner layer for cleaning and drying purposes. All this results from the design which minimizes the areas of attachment between the outer layer and the inner diaper layer.

BRIEF DESCRIPTION OF THE DRAWINGS

FIG. 3 is an view of a flattened diaper showing the inner layer.

FIG. 4 is a side view of a flattened diaper showing the looser fabric of the inner layer.

FIG. 5 is a relaxed side view showing separation of the layers, and demonstrating the results of a greater resiliency in the elastic of the outer layer.

FIG. 6 is a sectional view taken along line 6—6 of FIG. 2, and demonstrating the separation of the fabric layers at the sides of the diaper.

FIG. 7 is a sectional view taken along line 7—7 of FIG. 2, and demonstrating a preferred means for attachment of the layers at the forward end.

FIG. 8 is a sectional view taken along line 8—8 of FIG. 2, and demonstrating a preferred means for attachment of the layers at the rearward end, while showing an additional inclusion of elastic material therein.

DESCRIPTION OF THE PREFERRED EMBODIMENT

Figure 1:
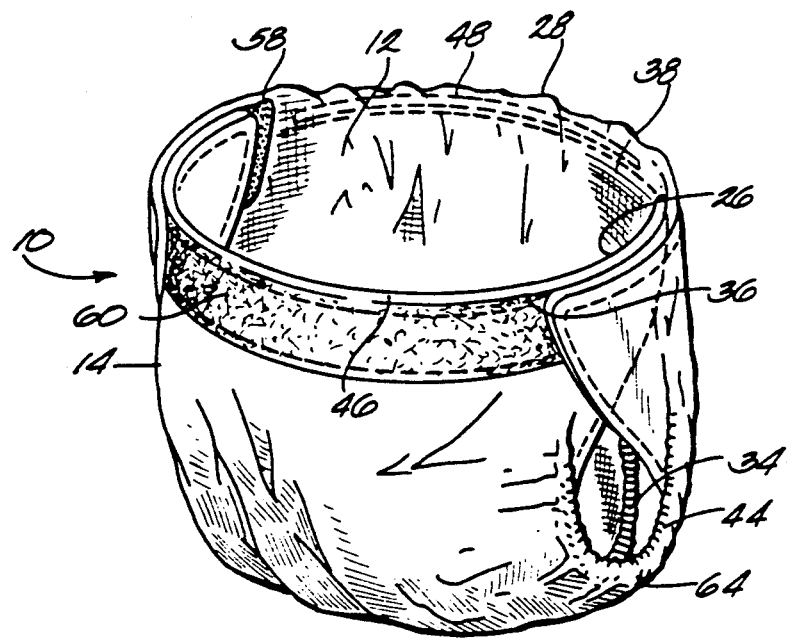
FIG. 1 is a view showing how the diaper is secured for wearing, displaying the outer layer, and showing hook fastener material at one end.

The preferred embodiment of the diaper has the features as disclosed in FIGS. 1 through 8. The diaper disclosed has separable fabric layers, with all the advantages provided by such a design, such as more thorough washability, improved drying times, and better breathability for preventing diaper rash. Additionally, this embodiment incorporates elastic into the midportions of the sides of the diaper, and across the rearward end. The greater resiliency of the elastic of the midportions of the sides of the outer layer over the corresponding elastic of the inner layer provides a more relaxed and looser inner layer, such as can be folded backwards or forwards as needed. There are many other features and advantages that can be incorporated to the basic design of this diaper, the layer separation making possible separate adjustments which can be used to improve the sizing and fit. The figures only depict the preferred embodiments of the invention by way of illustration of the best mode contemplated in carrying it out. It such should be understood that the invention is capable of other and different embodiments, and various details could be added or discarded without departing from the invention. The drawings and this description of the preferred embodiment are to be considered as illustrative in nature, and not restrictive.

Throughout their use in various figures and throughout the discussion, the numbers used to refer to various aspects or features of the diaper will remain constant.

The present invention provides a diaper 10 that is a composite of an inner layer 12 and an outer layer 14. Referring to FIGS. 5 and 6, it is seen that the inner layer 12 has opposite surfaces, an inner-facing surface 16 which is disposed towards the wearer's body, and an outer-facing surface 18 which is disposed toward the outer layer. Likewise, the outer layer 14 has an inner-facing surface 20 and an outer-facing surface 22. The inner layer is formed of a moisture absorbent textile fabric, most preferably a diaper material such as cotton, and the outer layer is formed of a water resistant fabric of any suitable kind, most preferably a 100% waterproof nylon. The diaper material of the inner layer may itself be a composite containing strongly absorbent fibers 24 between its surfaces.

As best shown in FIG. 3, the inner layer is shaped as a rectangle, and has opposite ends, a forward end 26 and a rearward end 28, and opposite sides 30. In the preferred embodiment the inner layer has midportions 32, and is contoured such that the width of the diaper across the midportions is narrower than the width across the opposite ends. In the specific embodiment of the invention shown in the drawings, elastic material 34 is attached and extends along the midportions of the opposite sides of the inner layer.

Figure 2:
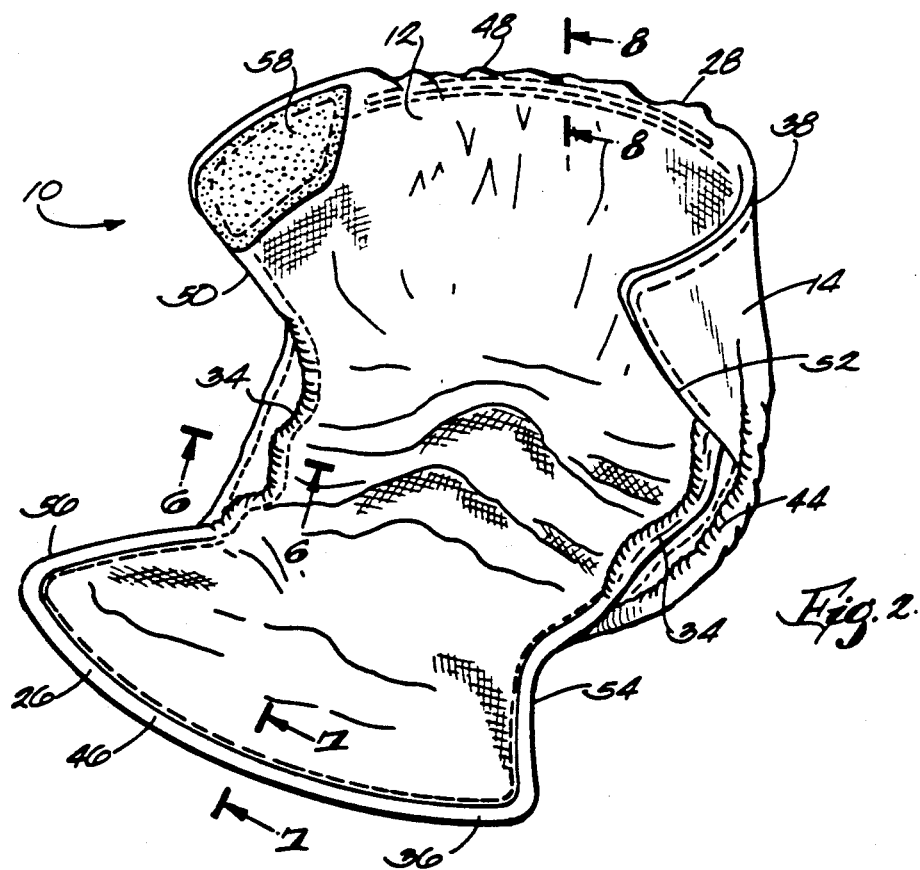
FIG. 2 is a view of the diaper partially opened to display the inner layer, and hook fastener material secured to another end.

As best shown in FIGS. 1 and 2, the outer layer of material is generally rectangular, with opposite ends, a forward end 36 and a rearward end 38, and opposite sides 40. In the illustrated embodiment the outer layer also has midportions 42, and is contoured such that the width of the outer layer at its ends is greater than the width at its midportions. In the illustrated arrangement, elastic material 44 is incorporated into the midportions of the opposite sides of the outer layer.

As best shown by FIGS. 5 and 6, the unique construction of the diaper is such that the composite layers are attached only along the forward edge 46 and the rearward edge 48 of the opposite ends, and optionally along edges 50, 52, 54 and 56 of the opposite sides that are nearest the opposite ends. With such a construction, the adjacent surfaces 18 and 20 of the different layers remain unattached and are separable from each other. The layers remain additionally unattached to one another at the area that corresponds to the midportions of their opposite sides.

As shown in FIGS. 5 and 6, the outer-facing surface 18 of the inner layer is freely separable from the inner-facing surface 20 of the outer layer, except for those areas at or near the opposite ends where the layers are attached along their edges. This construction provides the improved features of more efficient cleaning and drying, and also better breathability.

As is shown in FIGS. 1, 2 and 3, the illustrated embodiment of the diaper has hook fastener material 58, of the type commonly available under the trade name Velcro, attached to the opposite sides of one end, and complementary fastener material 60 attached across the opposite end. Hook fastener material provided in this manner improves the ease of use of the diaper. It also permits the user to adjust the diaper to fit a range of waist sizes. In the preferred embodiment, the hook fastener material is attached as a band 60 across the top of one end, so that the corners with the complementary hook faster material 58 can be pulled up about the waist as snugly as is required for a proper fit, and still hook fastener material will be available for attachment, regardless of where the corners fall across the first end.

A further feature of the illustrated embodiment, disclosed in FIGS. 4 and 5, is that the resiliency of the elastic incorporated into the midportions of the sides of the outer layer is greater than the resiliency of the elastic incorporated into the midportions of the sides of the inner layer. As a consequence, the inner layer 12 of the diaper is generally looser and more relaxed than the outer layer 14, allowing the diaper to be somewhat adjustable for size in length. Because the adjacent surfaces of the layers 18 and 20 are freely separable, this looser material of the inner layer can be pulled up 62 and folded in a manner to provide extra padding and absorbency as is useful. In the embodiment of the diaper as disclosed in FIGS. 3 and 6, it is seen additionally that the water retentive outer fabric layer 14 is slightly greater in width at its midportions 42 than the absorbent inner layer 12 is at its midportions 32. This extra width, in combination with the elastic material 44 incorporated into the outer layer, which extends parallel to the opposite sides, provides an added feature to the diaper. As demonstrated in the illustration of FIG. 1, 2 and 5, in such an embodiment the extra width of outer fabric is pulled up by the elastic material to aid in the formation of a moisture retentive barrier 64 about the wearers legs.

The elastic 44 in the outer layer serves another function as well, as can be seen in FIG. 5. When the diaper is opened and allowed to naturally flatten, the more resilient elastic of the outer layer contracts to a greater relative degree. This naturally leads to creation of a gap 66 between the inner-facing surface 20 of the outer layer and the outer-facing surface 18 of the inner layer. This gap can be further enhanced by attaching the complementary hook fastener materials 58 and 60 while the diaper is in an inverted condition. This natural gap formation greatly increases access to the diaper for both wash water and air of subsequent drying operations.

With reference to FIG. 8, it is seen that the preferred embodiment has elastic material 68 incorporated into the attachment of the fabric layers at the edge of the diaper disposed to the wearer's back 48. Such elastic material ensures a non-slipping, snug fit to the diaper. As is seen in FIG. 7, no elastic is incorporated into the attachment of layers 46 at the end portion disposed across the wearer's stomach. Any consequent bunching of material resulting from incorporating such elastic will be less likely to irritate or bind the skin of the wearer when incorporated to the edge disposed across the back of the wearer than it would if incorporated to the edge disposed across the wearer's front.

It is in any case evident that with a diaper of this invention, having a construction that provides for a separation of the fabric layers, there is greatly enhanced cleaning and drying efficiency over reusable diapers of previous designs.

I claim:

1. A composite diaper comprising an inner layer, at least a portion of the inner layer being formed of a moisture absorbent textile fabric, said inner layer having an inner-facing surface, an outer-facing surface, opposite ends, and opposite sides, the opposite sides of the inner layer each having a midportion intermediate the inner layer opposite ends, and the midportions of the opposite sides of the inner layer each having elastic material, and an outer layer formed of a water resistant fabric, said outer layer having an inner-facing surface, an outer-facing surface, opposite ends, and opposite sides, the opposite sides of the outer layer each having a midportion intermediate the outer layer opposite ends, and the midportions of the opposite sides of the outer layer each having elastic material, the opposite ends of the outer layer being joined to the opposite ends of the inner layer, the midportions of the opposite sides of the inner layer being freely separable from the midportions of the opposite sides of the outer layer, and the inner-facing surface of the outer layer being freely separable from the outer-facing surface of the inner layer except for the attachments of the inner layer and the outer layer at their opposite ends.

2. The composite diaper of claim 1 wherein the opposite sides of the outer layer each include opposite ends and the opposite sides of the inner layer each include opposite ends, and the opposite sides of the outer layer are joined to the opposite sides of the inner layer at their corresponding opposite ends, the midportions of the opposite sides of the inner layer being freely separable from the midportions of the opposite sides of the outer layer, and the inner-facing surface of the outer layer being freely separable from the outer-facing surface of the inner layer except for the attachment of the inner layer and the outer layer at their opposite ends and at the opposite ends of their opposite sides.

3. The composite diaper of claim 1 wherein the elastic material included in each of the midportions of the opposite sides of the outer layer is elongated and extends parallel to said opposite sides.

4. The composite diaper of claim 3 wherein the elastic material is spaced inwardly from the midportions of the opposite sides.

5. The composite diaper of claim 1 wherein hook fastener material is secured to the opposite sides of one end, and complementary hook fastener material is secured to the opposite end.

6. A composite diaper comprising an inner layer, at least a portion of the inner layer being formed of a moisture absorbent textile fabric, said inner layer having an inner-facing surface, an outer-facing surface, opposite ends, and opposite sides, the opposite ends and sides forming corners and the opposite sides of the inner layer each having a midportion intermediate the inner layer opposite ends, and an outer layer formed of a water resistant fabric, said outer layer having an inner-facing surface, an outer-facing surface, opposite ends, and opposite sides, the opposite ends and sides forming corners and the opposite sides of the outer layer each having a midportion intermediate the outer layer opposite ends, the midportions of the opposite sides of the outer layer and the midportions of the opposite sides of the inner layer including elastic material, the opposite ends of the outer layer being joined to the opposite ends of the inner layer, the midportions of the opposite sides of the inner layer being freely separable from the midportions of the opposite sides of the outer layer, means for releasably joining the corners at one end of the inner and outer layers to the opposite end of the inner and outer layers, and the inner-facing surface of the outer layer being freely separable from the outer-facing surface of the inner layer except for the attachments of the inner layer and the outer layer at their opposite ends.

7. The composite diaper of claim 6 wherein the resiliency of the elastic material included in the opposite sides of the outer layer is greater than the resiliency of the elastic material included in the opposite sides of the inner layer.

8. A composite diaper comprising an inner layer formed of diaper materials, said inner layer having an inner-facing surface, an outer-facing surface, opposite ends, and opposite sides, the opposite sides of the inner layer each having a midportion intermediate the inner layer opposite ends, and an outer layer formed of a water resistant fabric, said outer layer having an inner-facing surface, an outer-facing surface, opposite ends, and opposite sides, the opposite sides of the outer layer each having a midportion intermediate the outer layer opposite ends, the widths across the midportions of the inner layer and the outer layer being narrower than the widths across their opposite ends, the midportions of the opposite sides of the outer layer and the midportions of the opposite sides of the inner layer including elastic material, the opposite ends of the outer layer being joined to the opposite ends of the inner layer, the midportions of the opposite sides of the inner layer being freely separable from the midportions of the opposite sides of the outer layer, and the inner-facing surface of the outer layer being freely separable from the outer-facing surface of the inner layer except for the attachments of the inner layer and the outer layer at their opposite ends.

9. The composite diaper of claim 8 wherein the resiliency of the elastic material included in the opposite sides of the outer layer is greater than the resiliency of the elastic material included in the opposite sides of the inner layer.

10. A composite diaper comprising an inner layer formed of diaper material, said inner layer having an inner-facing surface, an outer-facing surface, opposite ends, and opposite sides, the opposite sides of the inner layer each having opposite ends and a midportion, and an outer layer formed of a water resistant fabric, said outer layer having an inner-facing surface, an outer facing surface, opposite ends, and opposite sides, the opposite sides of the outer layer each having opposite ends and a midportion, the widths across the midportions of the inner layer and the outer layer being narrower than the widths across their opposite ends, the midportions of the opposite ends of the outer layer being joined to the opposite ends of the inner layer, the opposite sides of the outer layer being joined to the opposite sides of the inner layer at their corresponding opposite ends, the midportions of the opposite sides of the inner layer being freely separable from the midportions of the opposite sides of the outer layer, the inner-facing surface of the outer layer being freely separably from the outer-facing surface of the inner layer except for the attachments of the inner layer and the outer layer at their opposite ends, and hook fastener material being secured to the opposite sides of one end, and complementary hook fastener material being secured to the opposite end.

11. The composite diaper of claim 10 wherein the resiliency of the elastic material included in the opposite sides of the outer layer is greater than the resiliency of the elastic material included in the opposite sides of the inner layer.

* * * * *

UNITED STATES PATENT AND TRADEMARK OFFICE
CERTIFICATE OF CORRECTION

PATENT NO. : 5,106,382
DATED : April 21, 1992
INVENTOR(S) : Donna Henry

It is certified that error appears in the above-identified patent and that said Letters Patent is hereby corrected as shown below:

Column 8, line 1, the word "ends" should read ---sides---.

Column 8, line 1, after the word "layer", insert ---and the midportions of the opposite sides of the inner layer including elastic material, the opposite ends of the outer layer---.

Column 8, Line 8, the word "separably" should read ---separable---.

Signed and Sealed this

Seventeenth Day of August, 1993

Attest:

BRUCE LEHMAN

Attesting Officer     Commissioner of Patents and Trademarks